United States Patent
Rombach

(10) Patent No.: US 8,579,972 B2
(45) Date of Patent: Nov. 12, 2013

(54) CONSTRUCTION OF AN INTRAOCULAR ARTIFICIAL LENS

(75) Inventor: Michiel Christiaan Rombach, Breda (NL)

(73) Assignee: Akkolens International B.V. (NL)

( * ) Notice: Subject to any disclaimer, the term of this patent is extended or adjusted under 35 U.S.C. 154(b) by 638 days.

(21) Appl. No.: 11/885,133

(22) PCT Filed: Mar. 9, 2006

(86) PCT No.: PCT/NL2006/050050
§ 371 (c)(1),
(2), (4) Date: Jul. 25, 2008

(87) PCT Pub. No.: WO2006/118452
PCT Pub. Date: Nov. 9, 2006

(65) Prior Publication Data
US 2009/0062912 A1    Mar. 5, 2009

(30) Foreign Application Priority Data

Mar. 9, 2005   (NL) .................................. 1028496
May 13, 2005   (NL) .................................. 1029041

(51) Int. Cl.
*A61F 2/16*     (2006.01)
(52) U.S. Cl.
USPC ........................................ 623/6.34; 623/6.49
(58) Field of Classification Search
USPC ............................................. 623/6.11–6.62
See application file for complete search history.

(56) References Cited

U.S. PATENT DOCUMENTS

| | | | |
|---|---|---|---|
| 3,305,294 A * | 2/1967 | Alvarez | 351/159.42 |
| 4,657,546 A * | 4/1987 | Shearing | 623/6.21 |
| 4,863,468 A | 9/1989 | Feinbloom et al. | |
| 4,994,082 A | 2/1991 | Richards et al. | |
| 5,443,506 A | 8/1995 | Garabet | |
| 5,824,074 A | 10/1998 | Koch | |
| 6,197,059 B1 * | 3/2001 | Cumming | 623/6.39 |
| 6,616,691 B1 * | 9/2003 | Tran | 623/6.11 |
| 7,615,056 B2 * | 11/2009 | Ayton et al. | 606/107 |
| 2002/0002404 A1 * | 1/2002 | Sarfarazi | 623/6.34 |
| 2002/0173847 A1 * | 11/2002 | Pham et al. | 623/6.26 |
| 2004/0158322 A1 * | 8/2004 | Shen | 623/6.33 |
| 2006/0241752 A1 * | 10/2006 | Israel | 623/6.34 |
| 2009/0062912 A1 * | 3/2009 | Rombach | 623/6.32 |
| 2010/0106245 A1 * | 4/2010 | Rombach et al. | 623/6.39 |

FOREIGN PATENT DOCUMENTS

| | | |
|---|---|---|
| EP | 0162573 | 11/1985 |
| NL | 1025622 | 9/2005 |
| WO | 2005084587 | 9/2005 |

* cited by examiner

*Primary Examiner* — Paul Prebilic
(74) *Attorney, Agent, or Firm* — The Webb Law Firm, P.C.

(57) ABSTRACT

This invention concerns an intraocular artificial lens with variable optical power which lens is comprised of two optical elements which can be shifted relatively to each other in a direction perpendicular to the optical axis wherein the optical elements have such a shape that they exhibit, in combination, different optical powers at different relative positions and positioning means for positioning the optical elements in the eye and driving means for at least one of the optical elements to execute a movement relative to the other optical element and whereby the positioning means provide for forcing the optical elements to a resting position.

1 Claim, 4 Drawing Sheets

CONSTRUCTION OF AN INTRAOCULAR ARTIFICIAL LENS

BACKGROUND OF THE INVENTION

1. Field of the Invention

This invention concerns an intraocular artificial lens with variable optical power comprising two optical elements mutually shiftable in a direction perpendicular to the optical axis wherein the optical elements have such a shape that they exhibit, in combination, different optical powers at different relative positions and comprising positioning means for positioning the optical elements in the eye and driving means for driving at least one of the optical elements to execute a movement relative to the other optical element.

2. Description of the Prior Art

Such a intraocular lens has been also described in the Dutch patent application 1025622.

The ciliary body of the eye of which the ciliary muscle forms a part is positioned just behind the iris and in front of the vitreous body of the eye. In the resting position the ciliary muscle has a relative large diameter and when contracting it contracts to a muscle with a smaller diameter. This muscle drives the accommodative function. The capsular bag is positioned within the ciliary muscle and the natural flexible lens of the eye is positioned in the capsular bag. The capsular bag is connected to the ciliary muscle by zonulea extending substantially radially.

The natural accommodation of the eye with a natural lens occurs as follows. During distant viewing the ciliary muscle is relaxed and has a relatively large diameter. Thus a pulling force is applied on the zonulae stretching the capsular bag resulting in a relatively flat lens. The natural state of the ciliary muscle results in distant viewing. The ciliary muscle contracts at distant viewing resulting in a smaller diameter. The zonulae relax and the natural lens resumes its natural more concave shape.

SUMMARY OF THE INVENTION

The present patent application describes the principle of application of two optical elements which are mutually shiftable in a direction perpendicular to the optical axis in an intraocular artificial lens. The application covers several basic measures for positioning, fixating and driving of such an intraocular artificial lens in the capsular bag after the natural lens has been removed. The optical elements can be moved relative to each other, driven by the natural ciliary muscle of the eye to obtain an accommodative function.

The aim of the invention is to provide an intraocular artificial lens wherein the natural accommodative functionality of the eye is approached as far as possible.

The aim is achieved in that the positioning means are adapted to urge the optical elements to a resting position . Thus a structure is created, just as with the natural lens, in which the intraocular artificial lens construction as a whole resumes its resting position in the absence of external force applied to it.

According to the first embodiment the optical elements are adapted to resume in a resting position with the optical power for viewing at close distance. This is the most common situation in our present society looking at a close distance for to reading or looking at a computer screen for instance.

In an alternative embodiment the optical elements are adapted to resume a resting position with an optical power for distant viewing. In this embodiment the elements are shifted away from the resting position at accommodation for close distant viewing.

Both embodiments utilize a structure for driving the artificial lens with some similarity to the driving mechanism of the natural eye lens.

Another embodiment provides the measure that the positioning means include stopping means active in at least one position. These stopping means can be situated at positions constructively attractive around the intraocular lens. The stopping means may be situated such that the elements are active at both ends of the working range so that they serve to define the area over which the optical elements can move.

Yet another embodiment provides the measure that the positioning means are adapted to urge the outer rim of capsular bag outwards and bring the rim in mechanical contact with the ciliary muscle. The capsular bag is, indirectly, connected to the ciliary muscle by flexible support ribbons extending in a radial direction. This measure connects the rim of the capsular bag to the ciliary muscle so that the movements of the ciliary muscle are directly transferred to the those of the optical elements so that a more direct coupling is obtained.

Another preferred embodiment provides the measure that the optical elements form a lens with the weakest optical dioptre power in their most overlapping position and a lens with the strongest dioptre optical power in their least overlapping position. This avoids the situation that at a large opening of the iris the quality of the viewing is impeded by glare.

An alternative embodiment provides the measure that the optical elements form a lens with the strongest dioptre optical power in their most overlapping position and a lens with the weakest dioptre optical power in their least overlapping position. This embodiment has a reduced size in the eye with certain designs of an artificial lens construction in the eye.

A next embodiment provides the measure that the positioning means are adapted to adjust the resting position of the optical elements after implantation in the capsular bag. The artificial lens is implanted during a surgical procedure. Often there is a need for some adjustability of the positioning means because the situation in the eye can not be determined precisely beforehand. Herewith it is possible to adjust the positioning means during the surgery according to the situation found. However, it is also possible to make the adjustment later, for example when the user has gained a few weeks of experience with the artificial intraocular lens. Aberrations observed during this period may then be corrected.

It is attractive to implement this embodiment by including a element in the positioning means of which a size is adjustable. This adjustability is obtained by including two components in the element which are mutually connectable in various positions, for example by providing one of the components of engageable patterns and to provide the other element of engagement means adapted to engage the patterns at different positions. It is also possible to utilize an element of which the length can be varied by an external factor. An example thereof is formed by an element made of a certain polymer which undergoes a further polymerisation through supply of energy and which changes its length during this further polymerisation. Another example is the application of so called memory metals which can permanently change their shape due to added energy, in the present application preferably laser light. An element with such a shape can be designed that it can change its length when changing its shape.

A first relatively simple embodiment provides the measure that the driving means include four levers of which the first pair is connected with the side of one of the optical elements en the second pair is connected with the other side of the other optical element and in which one of the levers of each pair is connected with a first part of the capsular bag moving in tandem with the ciliary muscle and both other levers of each pair are connected with a second moving part which moving in tandem with the ciliary muscle and which is situated opposite to the first part.

An alternative embodiment provides the measure that the driving means comprise a mainly rigid connecting element which is connected at one side with the optical element and which is adapted to be connected at the other side with a part of the capsular bag which moves in tandem with the ciliary muscle. This measure also provides a relatively simple construction which, in addition, provides a more direct coupling between the movement of the part of the capsular bag connected to the ciliary muscle and said optical element.

It is clearly also possible to make the rigid connection element so rigid that the whole component has a transmission function, so that no additional guiding means are necessary. This makes the rigid component overly bulky. An attractive way to prevent this is to connect the optical elements at the opposite side by a connecting component to the capsular bag.

Such a connecting component can have the configuration of a sliding construction or a hinging construction. It is preferable to have the positioning means comprise a flexible connecting element which is situated at the side opposite the rigid connecting element, which is connected to the optical element and which is designed such that that it can be connected with the rim of the capsular bag which moves in tandem with the ciliary muscle. Hence a supporting component is obtained which is light in weight which enables a very simple and effective construction.

As mentioned above, the invention requires the presence of a connection between the connecting components and the part of the capsular bag which moves in tandem with the ciliary muscle. To establish such a connection the rigid and flexible components have anchors, also known as "haptics" at the side opposite to the side at which the components are attached to the optical element which anchors allow a connection with the part of the capsular bag moving in tandem with the ciliary muscle. These anchors can be an integrated part of the rigid or flexible connecting components.

An intraocular lens must be implanted during a surgical procedure. This implies that during implantation the ciliary muscle is relaxed. The intraocular lens according to the first embodiment will—as a result of the positioning means which urge the construction to a resting position—be in the resting position. Then the intraocular lens has its highest optical power and the driving means are contracted. During the implantation of the intra ocular artificial lens there might be insufficient connection between the rigid and flexible connecting components, the anchors and the rim of the capsular bag which moves in tandem with the ciliary muscle. Such a connection is required to connect the connecting components and the part of the capsular bag which moving in tandem with the ciliary muscle to enable proper functioning of the accommodating intraocular lens. To provide such a contact a further embodiment provides for the feature that the intraocular lens comprises fixation elements which are active for a limited period and which enable contact between the rigid and flexible connecting components and the part of the capsular bag which moves in tandem with the ciliary muscle. These fixation elements connect the rigid and flexible connecting components and the part of the capsular moving in tandem with the capsular bag so that these parts are offered the possibility to grow together.

The measure above requires that the accommodative function is not blocked after the limited period during which the permanent connection grows. Therefore a further embodiment provides the measure that the fixating elements are made from a material dissolvable in the liquids present in the eye. It is assumed that the dissolution process takes a time sufficiently long to allow growing together of the connecting components and the part of the capsular bag which moves in tandem with the ciliary muscle.

In yet another embodiment a $\Omega$-shaped structure is included in each of the flexible connecting components. This $\Omega$-shaped structure can be simply manufactured by a milling or moulding procedure and it has been shown in calculations that this shape is well suited because of a favourable distribution of mechanical tensions. This is important because of tiring of the materials has to be prevented as much as possible.

A prefered embodiment of the invention includes stopping means. The $\Omega$-shaped structures described above offers the option to implement these stopping means as stopping shoulders provided in these $\Omega$-shaped structures. This is a simple measure for inclusion of stopping shoulders.

In an alternative construction the flexibility is obtained by the measure that the flexible connecting components include a longitudinal component extending substantially perpendicular to the direction of movement of the optical elements, connected at both ends to the anchor and which is connected to the optical element at an intermediate position. Such configuration appears to have attractive mechanical properties.

Modern technology and materials offer possibilities to manufacture a thin intraocular lens according to the invention. However, this leads to the problem that the lens may become overly flabby and optical surfaces may be deformed by forces exerted to it during the accommodative process. This will lead to deterioration of the optical quality of the lens resulting from the optical elements. This can be prevented by the measure to provide enforcing elements extending around the rim of the optical elements by which the elements will obtain the required rigidity.

Modern attachment technology offers the possibility that the enforced rim is manufactured from a different material compared to the material from which the optical elements are made. This offers the measure to choose materials with optimal specifications to match the specific requirements.

The capsular bag into which the optical elements are inserted may contact the optical and stick or tack to them or even grow together. This may affect the functioning of the accommodative function of the intraocular lens. To prevent this the anchors are fitted with spacer components extending in the direction of the optical axis and which keep the front side and back side of the capsular bag apart from the optical elements.

A specific embodiment offers the measure that the anchors have such a shape that they elastically adapt to changes in the diameter of the capsular bag. The capsular bag is a dynamic unit; it changes its shape and diameter as a consequence of the conditions of contraction or relaxation of the ciliary muscle.

The principle of this invention requires use of at least two optical elements. It has appeared to the inventor that these elements can be identical. This leads to enormous advantages from a manufacturing standpoint. It must be noted that this feature does not only refer to the optical elements but also to the to the components connected to the optical elements.

Clearly the two elements must be positioned rotated over two different axes. The optical elements can also have different shapes or the accommodative function of one of the optical elements can be superimposed on a lens of a fixed optical power which corrects the basic refraction of the eye. Then different optical element result.

The flexible connectors and anchors and the rigid connectors and anchors can be manufactured from the same material. This feature offers the opportunity to produce al these components by the same manufacturing process such as by lathing and milling or by molding.

It is possible to manufacture the optical elements and the other components from different materials so that the choice of materials can be optimized for each function.

It can be attractive, also in dependence of the chosen materials, to manufacture the elements separately to be connected later. This embodiment concerns also a method of manufacturing an intraocular artificial lens comprising at least two optical elements and means for positioning for positioning the optical elements in the capsular bag wherein both the optical elements are connected prior to implantation of the artificial lens in the capsular bag.

It is attractive that at least one of the connections between the optical elements, the flexible and rigid connectors and the anchors is obtained by a mechanical form fitting connection. Such a connection can be made simply and without the application of additional means.

This embodiment concerns also a method for the manufacturing an intraocular artificial lens comprising least two optical elements and positioning means to position the optical elements in the capsular bag wherein the optical elements are connected to the positioning means during surgery wherein the intraocular lens is positioned into the capsular bag.

It is also possible that at least one of the connections between the optical elements, the flexible and rigid connection components and the anchors comprises glued connection. The type of glue has to be selected carefully as not to affect the functionality of the lens.

An exceptional attractive embodiment is obtained when at least one of the connections between the optical elements, the flexible and rigid connection components and the anchors is obtained by repeated polymerization of the materials.

Another option is that at least one of the connections between the optical elements, the flexible and rigid connection components and the anchors is obtained by a welded connection. Laser and ultrasonic technologies are examples of such welding technologies.

It is also possible that at least one of the connections between the optical elements, the flexible connecting components and the rigid connecting components and the anchors is formed by a moulded connection. It is possible to use the same or to use different materials for the various elements and components.

When form fitting connections are applied the connections should be preferably possible at various relative positions. This offers the opportunity to vary the relative position of the optical elements and the option to adapt the optical specification to the condition of the wearer. Such a process can take place during implantation of the intraocular artificial lens. This invention concerns also the working method where during implantation the size of the capsular bag is determined and where the optical elements with the positioning means are connected according to said measurement.

After implantation the anchors have to be fixatated to the part of the capsular bag that moves in tandem with the ciliary muscle. It is assumed that the anchors grow together with the tissue of the capsular bag. It is an option to provide the anchors with a roughened or corrugated surface to stimulate this growing process. The term roughened and corrugated include extensions with other shapes or other surface area increasing patterns.

Additionally it should be pointed out that for the application of the features of the present invention the optical elements must be moved over a certain distance to create sufficient difference in optical power between the end postions. It could be the case that the change in internal diameter of the ciliary muscle is insufficient for the application of this invention.

This can be solved in principle by application of a lever system which converts small movements of the ciliary muscle into a large movement of the optical elements.

It is also possible to utilize other forms of added energy such as micro-machines which are included in the bloodstream or which react to electric potentials or to the ciliary muscle or to movements of the eyelid. The ciliary muscle or the direction of vision as represented by the position of the eyeball or the iris can be utilized to control of the movements of the optical elements. Other sources of information for the control or for energy, such as energy to drive the system such as energy from light are not excluded.

DETAILED DESCRIPTION OF THE PREFERRED EMBODIMENTS

Figure 1:
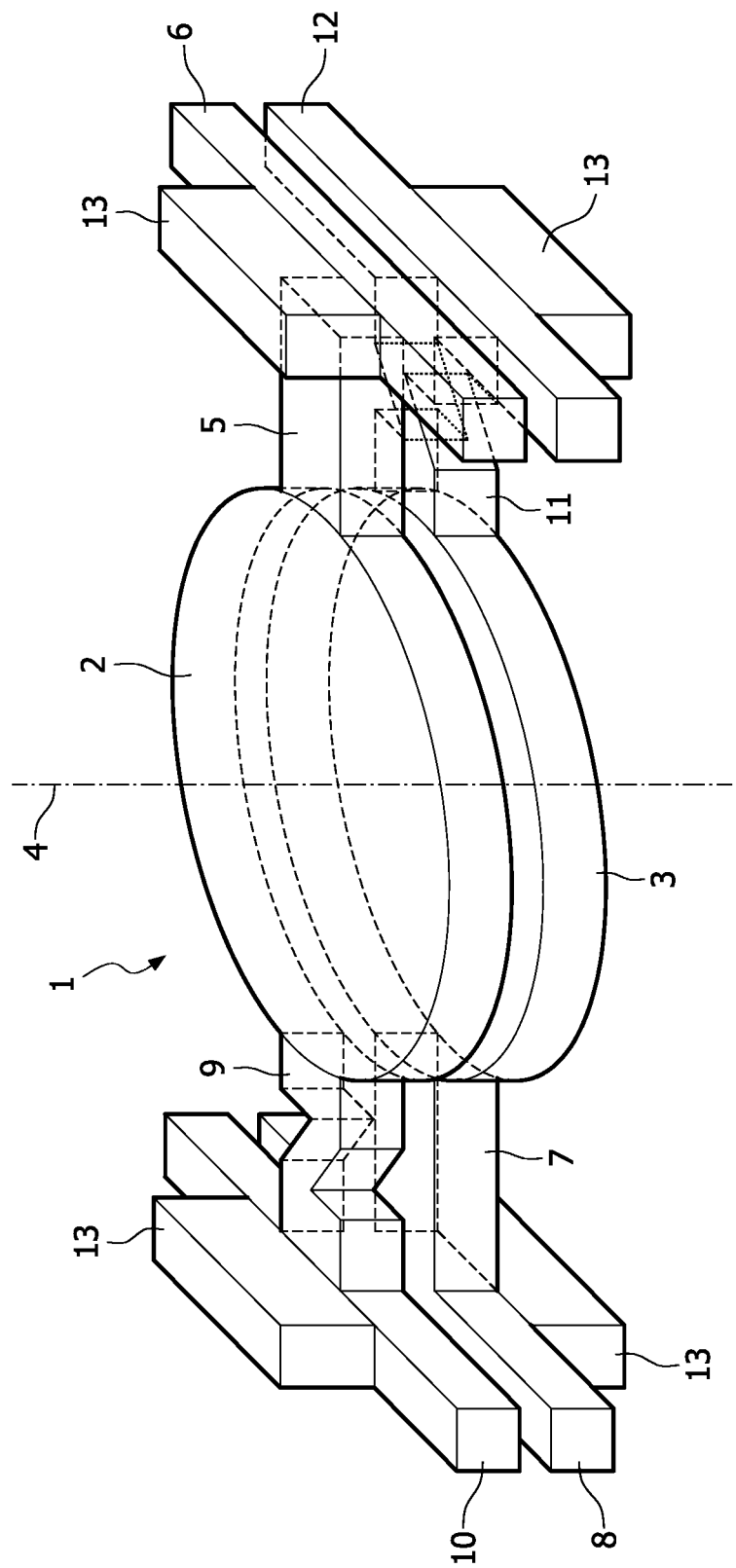
FIG. 1: A perspective diagram for explanation of the present invention.

FIG. 1 shows a perspective diagram of the intraocular artificial lens according to the invention wherein the lens is designated with a 1 as a whole. The lens comprises two optical elements 2, 3 both positioned in the optical axis 4 of the lens. The optical characteristics of the lens 1 change with a mutual shift of the optical elements. The optical elements 2, 3 are separated. The elements may contact from an optics standpoint, but touch is less attractive from a biological standpoint in relation to deposits on the optical elements and possible tack.

The upper (anterior or posterior) optical element 2 is comiected to anchor 6 by a rigid connecting component 5 to attach the intraocular artificial lens in the capsular bag, the natural cavity in the eye for the lens. The lower (posterior or anterior) optical element 3 is connected to anchor 8 by a rigid connecting component 7. The anchors 6, 8 extend in opposite positions and they are adapted for attachment to the part of the capsular bag which moves in tandem with the ciliary muscle.

The optical element 2 is connected by the flexible connecting component 9 to the anchor 10 at the side opposite to the rigid connecting element. Also, the optical element 3 is connected by a flexible connecting component 11 to the anchor 12 at the side opposite to the rigid connecting element. The anchors 10 and 12 serve similarly to anchors 6 and 8 for support of optical elements 2, respectively 3. The flexibility of the flexible connecting components 9, 11 allows movement of the optical elements 2,3. The upper optical elements 2 will move in tandem with the movements of anchor 6 and with the movements of the part of the capsular bag connected thereto which moves in tandem with the ciliary muscle as a consequence of this configuration. Similarly, the optical element 3 will move in tandem with anchor 8. The optical elements will show a mutual linear movement according to this configuration. It is also possible to construct the connecting components in such a way that the optical elements will show a mutual rotating or composed movement. The centre of rotation may be situated outside of the optical elements in case of a design for rotational movements.

The pair of anchors 6, 12 can be connected and the pair and 8,10 can be connected in various ways. However, it is an option to leave the pairs disconnected. However, all anchors must be attached to the capsular bag.

The anchors 6, 8, 10, 12 have been fitted with an extension 13 to create a spacing between the capsular bag and the optical elements.

At last it is pointed out that this figure is a schematic representation and is intended to illustrate the various elements, their relative positions and their functions. The shape of the various elements can, and will in most cases, deviate significantly.

Figure 2:
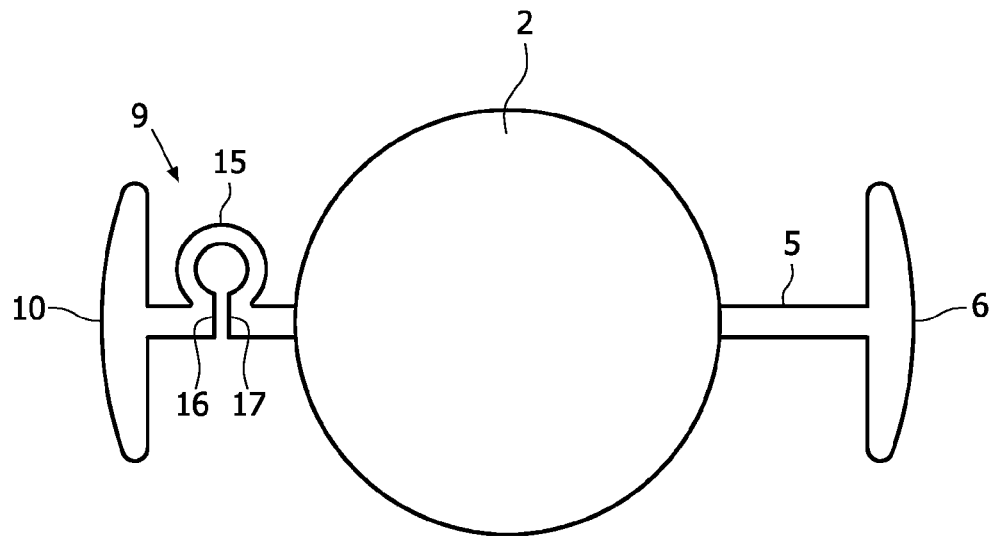
FIG. 2: A plan view of an optical element of an intraocular artificial lens according to the first embodiment.

FIG. 2 shows the construction of optical element 2 and the thereto attached components more in detail. This concerns in particular the flexible connecting component 9 which is fitted with the Ω-shaped component 15. The configuration of the Ω-shaped component provides a certain degree of flexibility. Other shapes such as screw shapes and spiral shapes are not excluded although it has been shown that the Ω-shaped component has advantages related to the prevention of the concentration of mechanical stress. The flexible element 9 is also fitted with two stopping elements 16 respectively 17 which define the resting position of the optical elements 2 and 3, but other configurations are not excluded.

Figure 3:
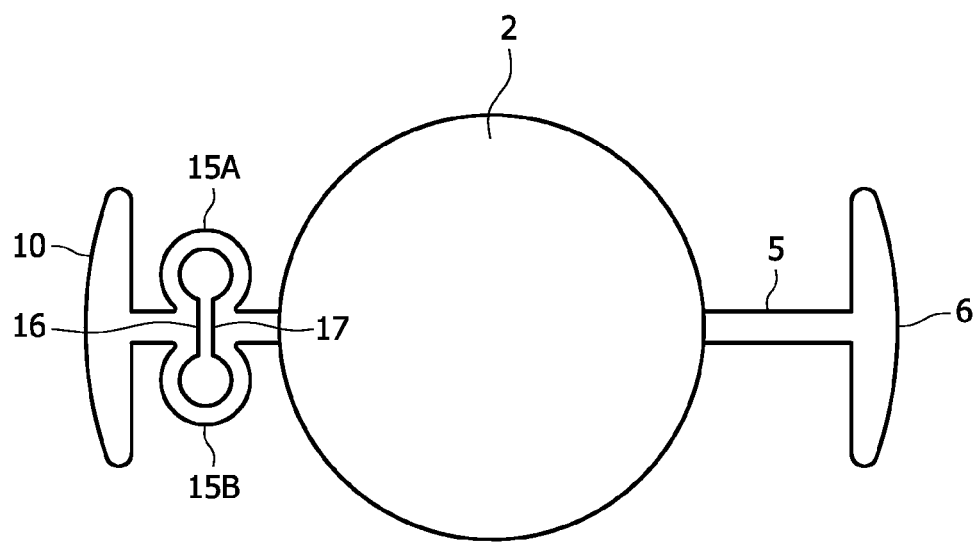
FIG. 3: A planar view comparable to FIG. 2 from the second embodiment.

Another variation is illustrated in FIG. 3, in which, rather than the Ω-shaped component 15, two of such configurations 15A and 15B, both positioned in the same plane, are applied. In this configuration possible sidelong forces are compensated so that only forces acting lengthwise along the flexible connecting component remain.

Figure 4:
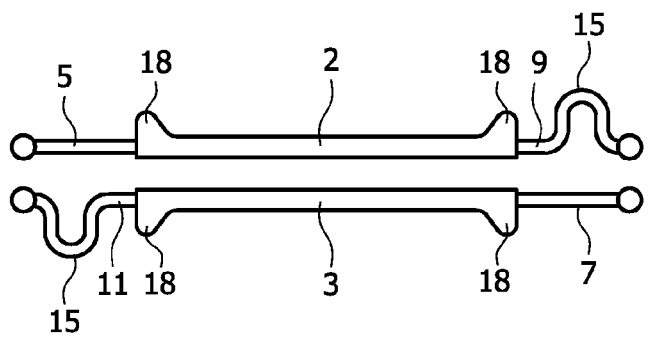
FIG. 4: A a side elevational view parallel to the optical axis of an intraocular artificial lens according to another embodiment.

A variation in which the optical elements 2, 3 are made so thin that the elements have insufficient rigidity is illustrated in FIG. 4. The optical elements 2,3 are both fitted with a thickened support 18 along the rim to prevent non-defined positions. Also, the loop of the Ω-shaped component extends into a plane parallel to the optical axis. It is also then possible to apply two loops situated in the same plane.

Figure 5:
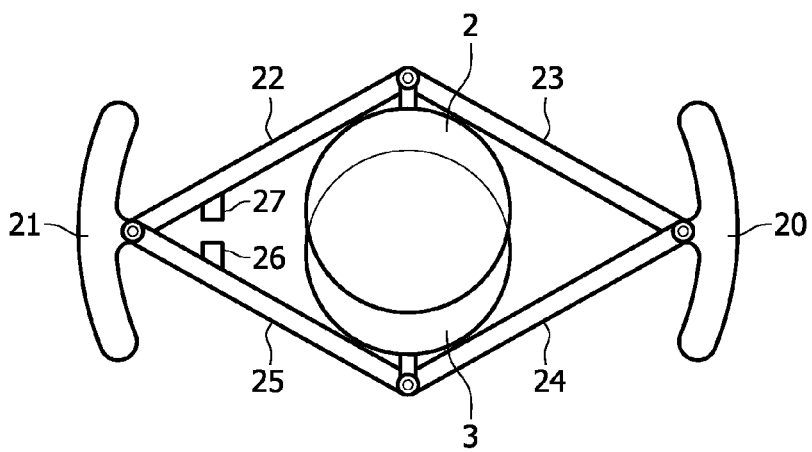
FIG. 5: A perspective view of another embodiment of an intraocular artificial lens in yet another embodiment of the invention.

An alternative approach for the suspension of the optical elements is illustrated in FIG. 5. The ciliary muscle moves two diagonally and oppositionally situated anchors 20, 21 connected by four levers 22, 23, 24, 25 which are positioned in the shape of a lozenge. Hinges are included between each of the levers and the anchors and between levers 22 23 and bewteen levers 24,25. The last hinges are also connected to optical element 2, respectively 3. Movement of anchors 20 and 21 will result in mutual movement of optical elements 2 and 3. No flexible elements are included in this embodiment when compared to the preferred embodiment. However, stopping shoulders 26, 27 can be included to define the resting position. Additional stopping shoulders can be included to define the position at the other extreme of the movement.

Figure 6:
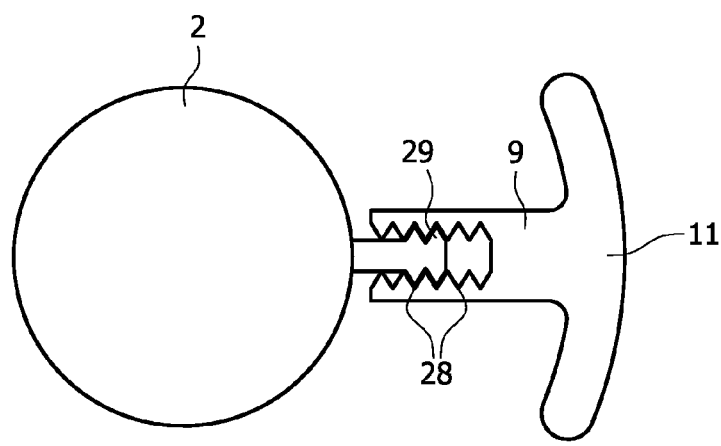
FIG. 6: A planar view of a further embodiment of an intraocular artificial lens according to the present invention.

An option for the connection between the optical elements and the rigid connecting component is shown in detail in FIG. 6. Herein an adjustment or adaptation between both elements 2 respectively 9 is possible. The rigid connecting component includes a number of notches 28 which have been adapted to engage a number of protuberances 29 attached to the optical element. It is possible to connect the optical element with the rigid connecting component at a various mutual positions through a larger number of notches. This measure enables adaptation of the mutual position of both optical elements in the resting position and so the optical power at the resting position. This measure provides the option to perform this adaptation in a later stage, for example during the surgery for the positioning of the lens.

Figure 7:
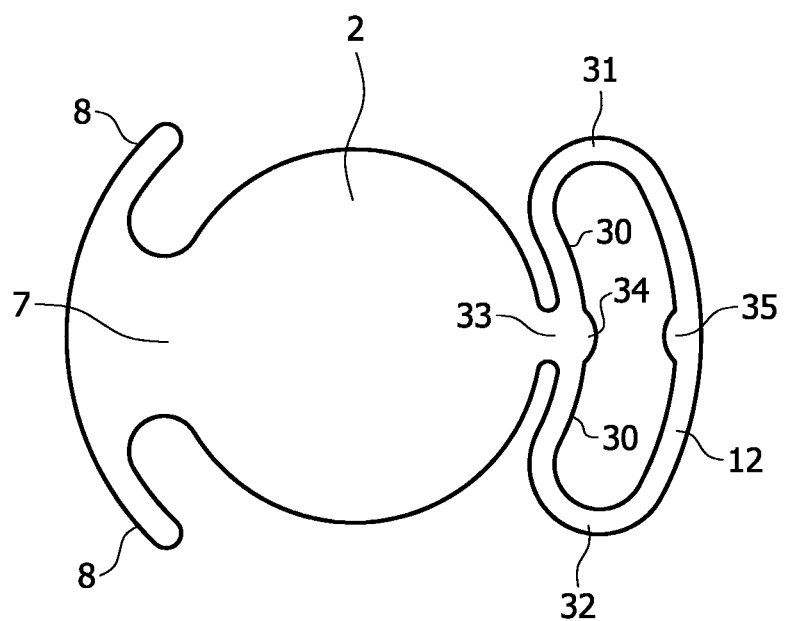
FIG. 7: A planar view of a specific embodiment of the invention.

An alternative configuration of a flexible connecting component and the connected anchor is provided in FIG. 7, in which only one optical element is presented. The connecting component includes an oblong component 30 which is positioned transversely to the axis of movement of the optical elements. This oblong connecting component 30 is at its extremities connected to connecting parts 31, 32 to anchor 12 and connected by a bridge 33 to the optical element 2. In this embodiment flexibility is provided by the oblong component 30 and the connecting parts 31 and 32. It should be pointed out that the connecting parts 31, 32 should be bended as to obtain an optimal distribution of forces. As a result an enclosed somewhat oval shape is formed by anchor 12, the connecting parts 31 and 32 and the oblong connecting component 30. Stopping elements 34, 35 can be included in the opening formed by 12, 30, 31 and 32. These stopping elements provide a similar function to the stoppers 16,17 presented in FIG. 2. It is evident that the intraocular lens according to the invention is composed of two optical elements which are mutually rotated over an angle of 180° in accordance with the configuration presented in FIG. 1.

It is shown above that adjustment can take place between the optical elements and the rigid connecting elements, but the adjustment function can also be incorporated between the rigid connecting component and the anchor or between the optical element and the flexible connecting element or between the flexible connecting element and the attached anchor. A combination of all these measures is also an option.

It is evident that also other configurations can be applied other than the presented configurations with a number of notches and protuberances. For example, parts of various length can be added to replace rigid or flexible connecting components.

Generally speaking it should be evident that combinations can be applied of the measures of the various embodiments described above. It is also possible to deviate from the embodiments described without violation of the protection of this invention.

The invention claimed is:

1. An intraocular artificial lens of variable optical power, comprising:
 two optical elements which are shiftable mutually in a direction perpendicular to an optical axis of said intraocular artificial lens, wherein the optical elements have such a shape that together they form a single lens, having different optical powers at different relative positions,
 driving mechanism including two mainly rigid connecting components each having a first side which is connected to an optical element for driving at least one of the optical elements for executing a movement relatively to the other optical element, and positioning mechanism for positioning each optical element in an eye, including two flexible connecting components each having a first side which is connected to each optical element at one end of said optical element that is opposite the rigid connecting component, wherein the driving mechanism is adapted to be connected to parts of the eye moving in tandem with a ciliary muscle of said eye;

wherein each positioning mechanism is adapted to urge each optical element to a resting position when each driving mechanism is inactive, wherein the two optical elements comprise an anterior optical element positioned over a posterior optical element, wherein the rigid connecting component of the anterior optical element is positioned over the flexible connecting component of the posterior optical element, and the flexible connecting component of the anterior optical element is positioned over the rigid connecting component of the anterior optical element, and wherein each flexible connecting component comprises an Ω-shaped structure.

* * * * *

UNITED STATES PATENT AND TRADEMARK OFFICE
CERTIFICATE OF CORRECTION

PATENT NO. : 8,579,972 B2  Page 1 of 1
APPLICATION NO. : 11/885133
DATED : November 12, 2013
INVENTOR(S) : Michiel Christiaan Rombach It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 963 days.

Signed and Sealed this
Twenty-second Day of September, 2015

Michelle K. Lee
*Director of the United States Patent and Trademark Office*